(12) United States Patent
Simpson et al.

(10) Patent No.: US 8,721,564 B2
(45) Date of Patent: *May 13, 2014

(54) GUIDE WIRE WITH CORE HAVING WELDED WIRE SEGMENTS

(71) Applicant: Abbott Cardiovascular Systems Inc., Santa Clara, CA (US)

(72) Inventors: John A. Simpson, Carlsbad, CA (US); Michael Plattner, Riverside, CA (US); Frank Manning, Temecula, CA (US); Ryan Grandfield, Murrieta, CA (US); Wayne E. Cornish, Fallbrook, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/892,959

(22) Filed: May 13, 2013

(65) Prior Publication Data

US 2013/0253374 A1    Sep. 26, 2013

Related U.S. Application Data

(60) Division of application No. 13/208,623, filed on Aug. 12, 2011, now Pat. No. 8,454,537, which is a division of application No. 12/405,971, filed on Mar. 17, 2009, now Pat. No. 7,998,090, which is a continuation-in-part of application No. 10/930,458, filed on Aug. 31, 2004, now abandoned.

(51) Int. Cl.
*A61B 5/00* (2006.01)

(52) U.S. Cl.
USPC .......................................................... 600/585

(58) Field of Classification Search
USPC .......................................................... 600/585
See application file for complete search history.

(56) References Cited

U.S. PATENT DOCUMENTS

| | | | |
|---|---|---|---|
| 4,358,658 A | 11/1982 | Van Blarigan et al. | |
| 5,124,529 A | 6/1992 | Nishikawa et al. | |
| 5,135,503 A | 8/1992 | Abrams | |
| 5,368,661 A | 11/1994 | Nakamura et al. | |
| 5,488,959 A | 2/1996 | Ales | |
| 6,306,105 B1 | 10/2001 | Rooney et al. | |
| 6,387,060 B1 * | 5/2002 | Jalisi | 600/585 |
| 6,602,208 B2 | 8/2003 | Jafari | |
| 6,645,159 B1 | 11/2003 | Burkett | |
| 6,669,652 B2 | 12/2003 | Anderson et al. | |

(Continued)

FOREIGN PATENT DOCUMENTS

WO    2006002199 A1    1/2006

*Primary Examiner* — Max Hindenburg
(74) *Attorney, Agent, or Firm* — Fulwider Patton LLP

(57) ABSTRACT

An intravascular guide wire having two core materials joined together without the use of a connector tube or sleeve, the core materials being stainless steel and psuedoelastic metal alloy, nitinol. The core materials are joined to each other through an intermediate transition piece made essentially of nickel, which is welded on either side to the two core materials. In a multi-segment intravascular guide wire, discrete, high modulus and medium modulus core portions of different materials are welded to a shapeable, low modulus distal core portion made of a third material having a flattened, shapeable section at a most distal end that is not welded to but made from the distal core portion, so the flattened, shapeable section can be deformed to create a steerable tip. Processes such as simultaneous resistance and friction welding can be used to join the core portions.

4 Claims, 5 Drawing Sheets

(56) References Cited

U.S. PATENT DOCUMENTS

| | | |
|---|---|---|
| 6,702,762 B2 | 3/2004 | Jafari et al. |
| 6,866,642 B2 | 3/2005 | Kellerman |
| 6,918,882 B2 | 7/2005 | Skujins et al. |
| 7,316,656 B2 | 1/2008 | Shireman et al. |
| 7,547,288 B2 | 6/2009 | Murayama et al. |
| 7,632,237 B2 * | 12/2009 | Murayama et al. ........... 600/585 |
| 8,454,537 B2 * | 6/2013 | Simpson et al. ............... 600/585 |
| 2003/0069520 A1 | 4/2003 | Skujins et al. |
| 2004/0030265 A1 | 2/2004 | Murayama et al. |
| 2004/0181176 A1 | 9/2004 | Jafari et al. |
| 2004/0260206 A1 | 12/2004 | Murayama et al. |
| 2007/0199607 A1 | 8/2007 | Murayama et al. |
| 2008/0171952 A1 | 7/2008 | Mishima |
| 2010/0199870 A1 | 8/2010 | Taig et al. |

* cited by examiner

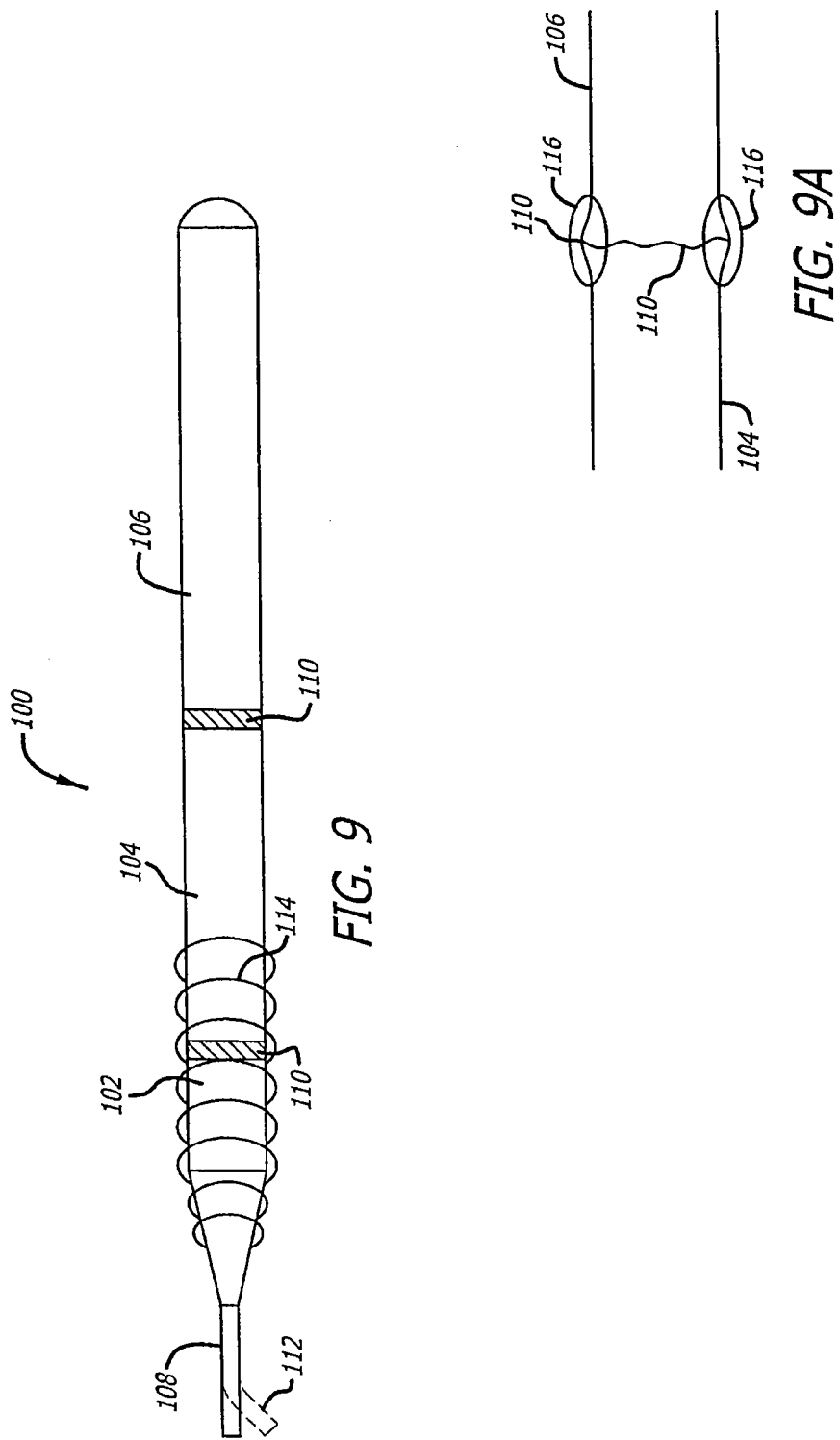

GUIDE WIRE WITH CORE HAVING WELDED WIRE SEGMENTS

CROSS-REFERENCE TO RELATED APPLICATIONS

This application is a continuation of U.S. Ser. No. 13/208,623 filed Aug. 12, 2011, which is a division of U.S. Ser. No. 12/405,971 filed Mar. 17, 2009, now U.S. Pat. No. 7,998,090 issued Aug. 16, 2011 and which is a continuation-in-part (CIP) of U.S. Ser. No. 10/930,458, filed Aug. 31, 2004, now abandoned, the entire contents of each of which are hereby incorporated by reference.

FIELD OF THE INVENTION

This invention relates to the field of medical devices, and more particularly to a guide wire for advancing a catheter within a body lumen in a procedure such as percutaneous transluminal coronary angioplasty (PTCA).

BACKGROUND OF THE INVENTION

In a typical PTCA procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guide wire is first advanced by itself through the guiding catheter until the distal tip of the guide wire extends beyond the arterial location where the procedure is to be performed. Then a catheter is mounted onto the proximal portion of the guide wire which extends out of the proximal end of the guiding catheter which is outside of the patient. The catheter is advanced over the guide wire, while the position of the guide wire is fixed, until the operative element on the catheter is disposed within the arterial location where the procedure is to be performed. After the procedure is performed, the catheter may be withdrawn from the patient over the guide wire or the guide wire may be repositioned within the coronary anatomy for an additional procedure.

Conventional guide wires for angioplasty, stent delivery, atherectomy and other intravascular procedures usually have an elongate core member with one or more segments near the distal end thereof which taper distally to smaller cross sections. A flexible body member, such as a helical coil or a tubular body of polymeric material, is typically disposed about and secured to at least part of the distal portion of the core member. A shaping member, which may be the distal extremity of the core member or a separate shaping ribbon which is secured to the distal extremity of the core member, extends through the flexible body and is secured to the distal end of the flexible body by soldering, brazing or welding; or an adhesive may be used in the case of a polymeric flexible body which forms a rounded distal tip. The leading tip is highly flexible in order not to damage or perforate the vessel. The portion behind the distal tip becomes increasingly stiff, the better to support a balloon catheter or similar device.

A major requirement for guide wires is that they have sufficient column strength to be pushed through a patient's vascular system or other body lumen without buckling. However, they must also be flexible enough to avoid damaging the blood vessel or other body lumen through which they are advanced. Efforts have been made to improve both the strength and flexibility of guide wires to make them more suitable for their intended uses, but these two properties are for the most part diametrically opposed to one another in that an increase in one usually involves a decrease in the other.

In order to fulfill these requirements, guide wires now typically include two different types of material joined together with a connecting tube, or sleeve, so that a proximal core will consist of a material having sufficient column strength and a distal core will be made of a flexible material to lead the advance through a body lumen. Currently, a nitinol hypotube or connecting tube is used as a sleeve to join a proximal stainless steel core to a nitinol distal core on certain types of guide wires. An example of this type of guide wire can be seen in, for example, U.S. Pat. Nos. 6,248,082 and 6,602,208 (Jafari). The reason that an external tube is used to achieve the connection is because direct welding of nitinol to stainless steel has proven to be difficult if not effectively impossible. Attempts to achieve such a weld are met with serious deficiencies in the resulting strength and unique behavioral properties of nitinol. Furthermore, cracking may occur at the interface between the two metal portions at the weld. However, when this problem is overcome by connection with an external connecting tube, the presence of the tube disadvantageously adds to the profile of the guide wire, tending to obstruct elements of the catheter that must slide along the guide wire during operation.

One prior solution to the general problem of connecting stainless steel to nitinol has been to insert an intermediate vanadium alloy transition piece between the stainless steel piece and the nitinol piece, welding the outer two metal pieces to the inner transition piece. However, in the context of microwelding very small metal pieces, such as portions of a guide wire that may measure between about 0.040 and 0.010 inches diameter at the section to be joined, even this solution may cause deficiencies in the strength and behavioral properties of nitinol due to the high temperature required to melt vanadium. It will be appreciated that welding small work pieces together provides less opportunity for heat to escape from the site of the weld, thus permitting heat buildup at the location of the weld to the detriment of the metal properties and the eventual uniformity and quality of the weld.

Thus, a need exists for an improved guide wire, and method for manufacture, that will address the needs of the prior art. It is believed that the present invention addresses these and other needs.

SUMMARY OF THE INVENTION

The present invention is directed to an intravascular guide wire having a stainless steel proximal portion joined to a nitinol distal portion without the use of an external tube or sleeve to reinforce the joint. As noted above, it is known that direct welding of stainless steel to nitinol is difficult if not impossible, in that attempts to do so are met with serious deficiencies in the resulting weld strength and unique behavioral properties of nitinol.

Accordingly, in each embodiment of the present invention, a transition piece formed essentially of nickel is utilized to effect the connection between the stainless steel proximal portion and the nitinol distal portion, as it appears that nickel will form a welded bond with both stainless steel and nitinol, without cracking or metal property alteration taking place at the oundaries between the welded metals. The preferred composition of the transition piece is effectively pure nickel, although alloying with different metals may be permitted to the extent that (a) this does not interfere with the ability of the resulting composition to form an essentially crack-free bond with the adjacent stainless steel and nitinol portions or (b) does not cause the melting temperature of the resulting composition to be elevated to a point where the heat required to form the weld removes or diminishes the unique characteristics of nitinol. In the preferred embodiment, welding may be performed by known methods of laser or friction welding, although other known forms of microwelding such as electron beam welding, and plasma arc welding may be used.

In different embodiments, the geometry of the transition piece may differ to provide different structural and strength characteristics and advantages, as desired. In a first embodiment, the transition piece has a simple cylindrical shape with flat ends that are normal to the guide wire longitudinal axis. In another embodiment, the ends of the cylindrical piece may be shaped to be convex or concave, to mate with the corresponding end faces of the proximal portion and the distal portion. Alternatively, flat ends of the cylindrical piece may be angled to the guide wire axis. In a further embodiment the transition piece may be shaped to be positioned between opposing end faces of the proximal and distal portions that are substantially parallel to the guide wire axis. In yet a further embodiment, the transition piece may be shaped to connect non-opposing end faces of the proximal and distal portions that are substantially parallel to the guide wire axis. Each of these alternative embodiments provides the opportunity to develop enhanced compressive, tension, and torsion strengths of the welded connection, by extending or reducing the length of the welded portion as needed. The overall torqueability and pushabiilty of the guide wire are thus improved over a conventional guide wire.

Further, the resulting connection has the advantage of not being positioned within a reinforcing sleeve, thereby reducing the outer profile of the guide wire at the position of the connection to permit unobstructed sliding of elements of the catheter surrounding the guide wire during operation.

The present invention further contemplates, in a preferred embodiment, a multi-segment intravascular guide wire having a discrete, proximal, high modulus core portion with proximal and distal ends made of a first material; a discrete, intermediate, medium modulus core portion with proximal and distal ends, wherein the proximal end is joined to the distal end of the proximal core portion, made of a second material; a discrete, shapeable, low modulus distal core portion made of a third material, having a flattened, shapeable section at a most distal end that is not welded to but is made from the same third material as the shapeable distal portion, and wherein the flattened, shapeable section can be permanently deformed by finger pressure to create a tip that can be steered through a patient's vasculature. The guide wire further includes a plurality of weld zones joining the discrete core portions together with the weld zone outside diameters blended into the outside diameters of the respective core portions.

The present invention is further directed to a preferred method for joining a multi-segment core intravascular guide wire, for example, in a fabrication procedure. This method includes providing multiple, discrete portions of the guide wire core made from different materials; axially aligning the discrete core portions; rotating one portion at a fixed speed; butting two core portions together while applying a fixed axial force; increasing rotation speed of the joined core portions; increasing axial force; increasing resistance weld energy; holding resistance weld energy constant; decreasing resistance weld energy; and decreasing rotational speed to zero.

These and other advantages of the invention will become more apparent from the following detailed description thereof and the accompanying exemplary drawings.

BRIEF DESCRIPTION OF THE DRAWINGS

FIG. 9 is a simplified side elevational view of a core-to-tip guide wire having welded core sections and a shaping ribbon integrated into the distal core section without welding.

FIG. 9A is a detailed view of a weld zone with upset material.

DETAILED DESCRIPTION OF THE PREFERRED EMBODIMENTS

Figure 1:
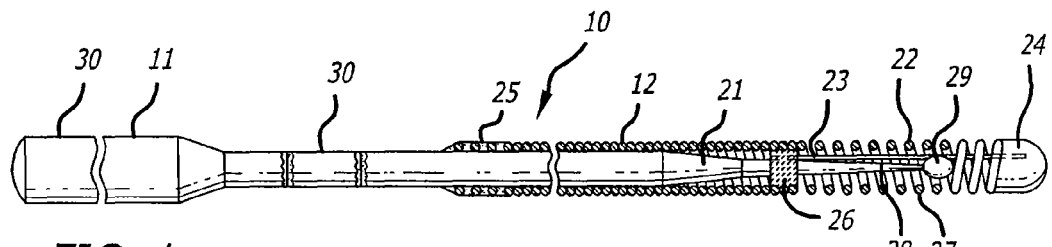
FIG. 1 is a side elevational view of one embodiment of an intraluminal guide wire, showing features of the invention.

FIG. 1 illustrates a guide wire 10 embodying features of the invention that is adapted to be inserted into a patient's body lumen, such as an artery or vein. The guide wire 10 comprises an elongated, relatively high strength proximal core section 11, and a relatively short flexible distal core section 12. The distal core portion 12 has at least one tapered section 21 which becomes smaller in the distal direction. A helical coil 22 is disposed about the distal core section 12 and is secured by its distal end to the distal end of shaping ribbon 23 by a mass of solder which forms rounded plug 24 when it solidifies. The proximal end of the helical coil 22 is secured to the distal core section 12 at a proximal location 25 and at intermediate location 26 by a suitable solder. The proximal end of the shaping ribbon 23 is secured to the distal core portion 12 at the same intermediate location 26 by the solder. Preferably, the most distal section 27 of the helical coil 22 is made of radiopaque metal, such as platinum or platinum-nickel alloy, to facilitate the fluoroscopic observation thereof while it is disposed within a patient's body. The most distal section 27 of the coil 22 should be stretched about 10 to about 30% in length to provide increased flexibility.

The most distal part 28 of the distal core section 12 is flattened into a rectangular cross-section and is preferably provided with a rounded tip 29, e.g., solder, to prevent the massage of the most distal part through the spacing between the stretched distal section 27 of the helical coil 22.

The exposed portion of the elongated proximal core section 11 should be provided with a coating 30 of lubricous material such as polytetrafluoroethylene (sold under the trademark Teflon® by Du Pont, de Nemours & Co.) or other suitable lubricous coatings such as other fluoropolymers, hydrophilic coatings and polysiloxane coatings.

The elongated proximal core section 11 of the guide wire 10 is generally about 130 to about 140 cm in length with an outer diameter of about 0.006 to 0.018 inch (0.15-0.45 mm) for coronary use. Larger diameter guide wires, e.g. up to 0.035 inch (0.89 mm) or more may be employed in peripheral arteries and other body lumens. The lengths of the smaller diameter and tapered sections can range from about 1 to about 20 cm, depending upon the stiffness or flexibility desired in the final product. The helical coil 22 may be about 3 to about 45 cm in length, preferably about 5 to about 20 cm, has an outer diameter about the same size as the outer diameter of the elongated proximal core section 11, and is made from wire about 0.001 to about 0.003 inch (0.025-0.08 mm) in diameter typically about 0.002 inch (0.05 mm). The shaping ribbon 23 and the flattened distal section 28 of distal core section 12 have generally rectangularly shaped transverse cross-sections which usually have dimensions of about 0.0005 to about 0.006 inch (0.013-0.152 mm), preferably about 0.001 by 0.003 inch (0.025-0.076 mm).

The distal core section 12 is preferably made of nitinol, which is a psuedoelastic alloy material preferably consisting essentially of about 30 to about 52% titanium and the balance nickel and optionally up to 10% of one or more other alloying elements. The other alloying elements may be selected from the group consisting of iron, cobalt, vanadium, platinum, palladium and copper. The alloy can contain up to about 10% copper and vanadium and up to 3% of the other alloying elements. The addition of nickel above the equiatomic amounts with titanium and the other identified alloying elements increases the stress levels at which the stress induced austenite-to-martensite transformation occurs and ensures that the temperature at which the martensitic phase thermally transforms to the austenitic phase is well below human body temperature (37 degrees C.) so that austenite is the only temperature stable phase at body temperature. The excess nickel and additional alloying elements also help to provide an expanded strain range at very high stresses when the stress induced transformation of the austenitic phase to the martensitic phase occurs. Moreover, it is known that heating nitinol excessively can change the pseudoelastic behavior, the martensite transitions temperatures, and even the shape memory. Therefore, heat input into the nitinol should be carefully controlled.

A presently preferred method for making the pseudoelastic distal core section is to cold work, preferably by drawing, a rod having a composition according to the relative proportions described above and then heat treating the cold worked product while it is under stress to impart a shape memory thereto. Typical initial transverse dimensions of the rod are about 0.045 inch to about 0.25 inch. Before drawing the solid rod, it is preferably annealed at a temperature of about 500 to about 750 degrees C., typically about 650 degrees C., for about 30 minutes in a protective atmosphere such as argon to relieve essentially all internal stresses. In this manner all of the specimens start the subsequent thermomechanical processing in essentially the same metallurgical condition so that products with consistent final properties are obtained. Such treatment also provides the requisite ductility for effective cold working.

The stress-relieved stock is cold worked by drawing in order to effect a reduction in the cross sectional area thereof of about 30 to about 70%. The metal is drawn through one or more dies of appropriate inner diameter with a reduction per pass of about 10% to 50%. Other forms of cold working can be employed such as swaging.

Following cold work, the drawn wire product is heat treated at a temperature between about 350 degrees C. and about 600 degrees C. for about 0.5 to about 60 minutes. Preferably, the drawn wire product is simultaneously subjected to a longitudinal stress between about 5% and about 50%, preferably about 10% to about 30% of the tensile strength of the material (as measured at room temperature) in order to impart a straight "memory" to the metal and to ensure that any residual stresses therein are uniform. This memory imparting heat treatment also fixes the austenite-martensite transformation temperature for the cold worked metal. By developing a straight "memory" and maintaining uniform residual stresses in the pseudoelastic material, there is little or no tendency for a guide wire made of this material to whip when it is torqued within a patient's blood vessel. The term "whip" refers to the sudden rotation of the distal tip of a guide wire when the proximal end of the guide wire is subjected to torque.

An alternative method for imparting a straight memory to the cold worked material includes mechanically straightening the wire and then subjecting the straightened wire to a memory imparting heat treatment at a temperature of about 300 degrees to about 450 degrees C., preferably about 330 degrees C. to about 400 degrees C. The latter treatment provides substantially improved tensile properties, but it is not very effective on materials which have been cold worked above 55%, particularly above 60%. Materials produced in this manner exhibit stress-induced austenite to martensite phase transformation at very high levels of stress but the stress during the phase transformation is not nearly as constant as the previously discussed method. Conventional mechanical straightening means can be used such as subjecting the material to sufficient longitudinal stress to straighten it.

Because of the extended strain range under stress-induced phase transformation which is characteristic of the pseudoelastic material described herein, a guide wire having a distal portion made at least in substantial part of such material can be readily advanced through tortuous arterial passageways. When the distal end of the guide wire engages the wall of a body lumen such as a blood vessel, it will pseudoelastically deform as the austenite transforms to martensite. Upon the disengagement of the distal end of the guide wire from the vessel wall, the stress is reduced or eliminated from within the pseudoelastic portion of the guide wire and it recovers to its original shape, i.e., the shape "remembered" which is preferably straight. The straight "memory" in conjunction with little or no nonuniform residual longitudinal stresses within the guide wire prevent whipping of the guide wire's distal end when the guide wire is torqued from the proximal end thereof. Moreover, due to the very high level of stress needed to transform the austenite phase to the martensite phase, there is little chance for permanent deformation of the guide wire or the guiding member when it is advanced through a patient's artery.

The present invention provides a guide wire which exhibits, at the distal portion, pseudoelastic characteristics to facilitate the advancement thereof in a body lumen. The distal guiding portion exhibits extensive, recoverable strain resulting from reversible, stress induced phase transformation of austenite to martensite at exceptionally high stress levels which greatly minimizes the risk of damage to arteries during the advancement therein.

The high strength proximal portion of the guide wire generally is significantly stronger, i.e., higher ultimate tensile strength, than the pseudoelastic distal portion. Suitable high strength materials include 304 stainless steel which is a conventional material in guide wire construction. Other high strength materials include nickel- cobalt-molybdenum-chromium alloys such as commercially available MP35N alloy.

Turning now to the connection between the stainless steel proximal portion 11 and the nitinol distal portion 12 of the guide wire, it has been found that connecting these two portions together by welding each to opposite ends of an intermediate transition piece formed from nickel achieves the desired connection without causing deficiencies in the strength and behavioral properties of the distal nitinol portion. While effectively unalloyed nickel is preferred for the transition piece, alloying the nickel with, for example, titanium, cobalt, copper or iron, to a degree which does not alter its ability to continuously form an essentially crack-free welded bond with the stainless steel proximal portion and nitinol distal portion, is permissible under alternative embodiments.

Figure 2A:
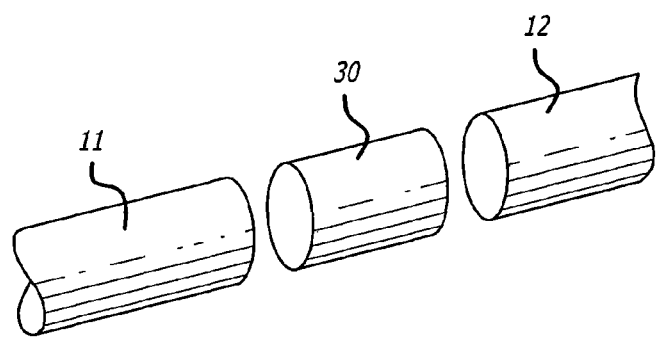
FIG. 2A is a fragmented perspective view of a portion of the guide wire of FIG. 1, showing a connection between proximal and distal portions via a cylindrical transition piece with flat ends.
Figure 2B:
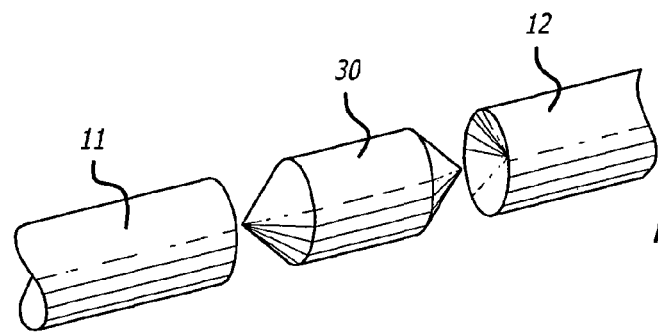
FIG. 2B is a fragmented perspective view of a portion of the guide wire of FIG. 1, showing a connection between proximal and distal portions via a cylindrical transition piece with concave ends.
Figure 2C:
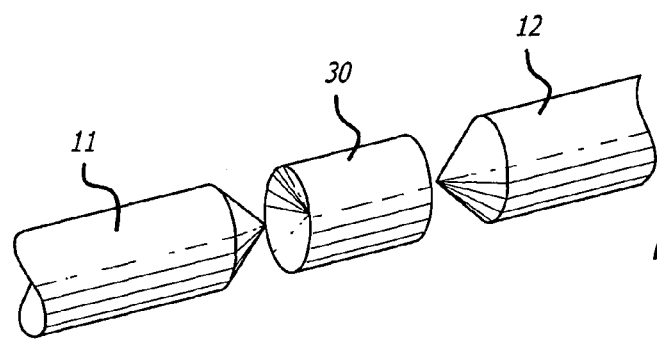
FIG. 2C is a fragmented perspective view of a portion of the guide wire of FIG. 1, showing a connection between proximal and distal portions via a cylindrical transition piece with convex ends.

In a preferred embodiment, exemplified in FIGS. 1 and 2, a butt weld may be used at each end of the transition piece 30 which may be cylindrically shaped. The transition piece 30 advantageously may have an aspect ratio (i.e., ratio of length to diameter) of between 0.5 and 3, preferably greater than 1.0. Furthermore, as seen in FIGS. 2B and 2C, the transition piece 30 may have a conical or a dome shaped end that is convex or concave. Likewise, the interface surface of the proximal or distal portion 11,12 has a complementary mating shape. Welding may be achieved by known methods of microwelding, such as friction welding, laser welding, electron beam welding, and plasma arc welding. Examples of known welding methods are described in U.S. Pat. No. 6,729,526 (friction welding), U.S. Pat. No. 4,358,658 (laser welding), and U.S. Pat. No. 5,951,886 (electron beam welding), the contents of which are incorporated herein by reference. In one preferred embodiment, friction welding is preferred as providing a high degree of precision and control. In another preferred embodiment, laser welding may be preferred as also providing a high degree of precision and control.

Figure 3:
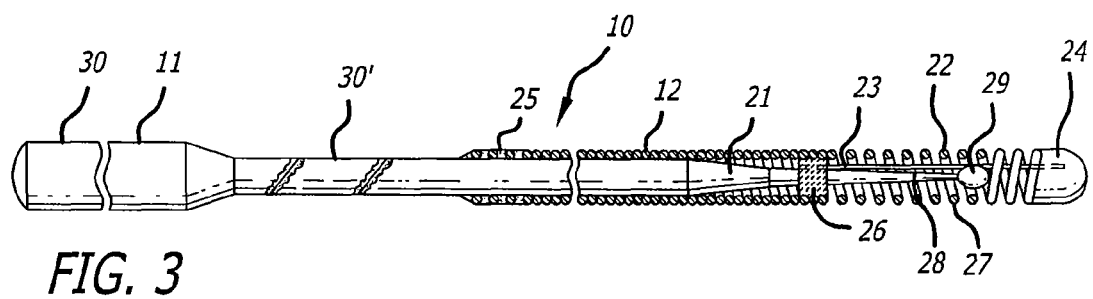
FIG. 3 is a side elevational view of another embodiment of an intraluminal guide wire, showing features of the invention.
Figure 4:
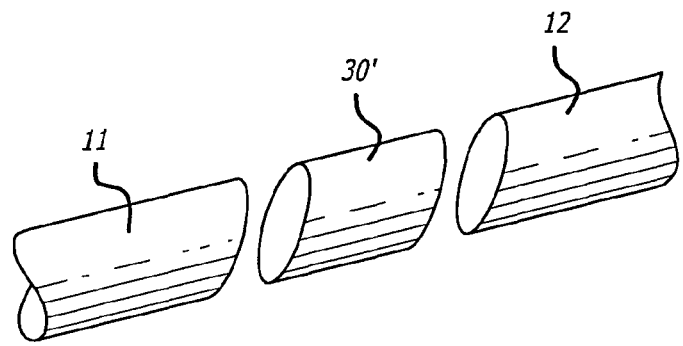
FIG. 4 is a fragmented perspective view of a portion of the guide wire of FIG. 3, showing a connection between proximal and distal portions.

In an alternative embodiment, exemplified in FIGS. 3 and 4, transition piece 30' may be shaped to contact the outer metal portions 11, 12 at an angle oblique to the longitudinal guide wire axis between about 30 degrees and 60 degrees, preferably 45 degrees, to provide a larger area of contact for opposing welded surfaces. It will be appreciated that friction welding may not be possible under these conditions, but laser welding will be a preferred method, giving rise to a connection with greater surface contact between the welded parts than the previous embodiment, and thus greater tensile, compressive, and torsional resistance characteristics.

Figure 5:
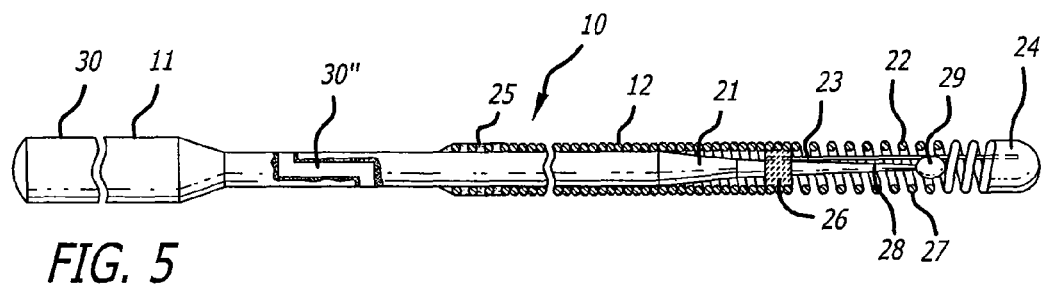
FIG. 5 is a side elevational view of a further embodiment of an intraluminal guide wire, showing features of the invention.
Figure 6:
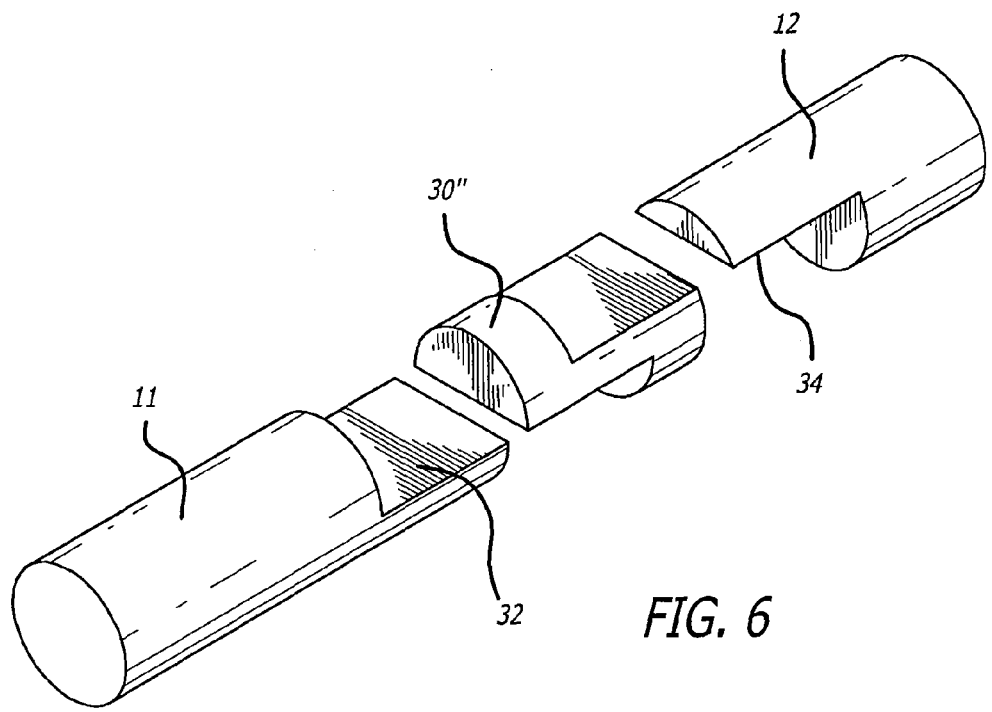
FIG. 6 is a fragmented perspective view of a portion of the guide wire of FIG. 5, showing a connection between proximal and distal portions.

In a further alternative embodiment, exemplified in FIGS. 5 and 6, the transition piece 30" may be shaped to fit between the outer metal portions 11, 12 which are shaped to provide a connection substantially between a horizontal surface 32 of the proximal portion and an opposing horizontal surface 34 of the distal portion. This configuration may be adapted to have the advantage of providing an even larger area of contact between the juxtaposed parts than that of the embodiment of FIGS. 3 and 4. A profile view of the transition piece 30" gives the appearance of a zigzag shape.

Figure 7:
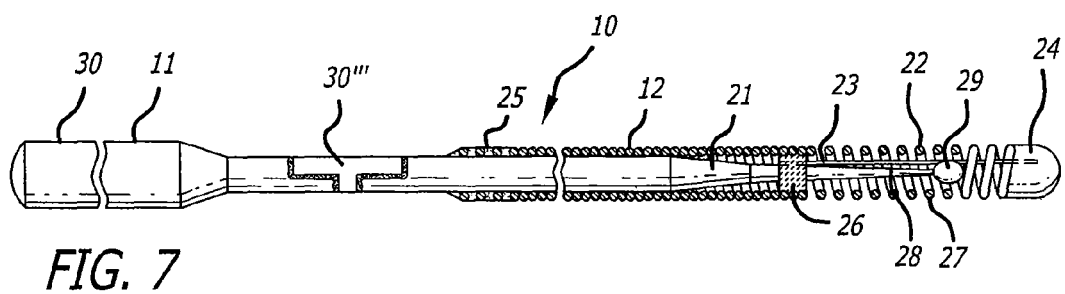
FIG. 7 is a side elevational view of yet a further embodiment of an intraluminal guide wire, showing features of the invention.
Figure 8:
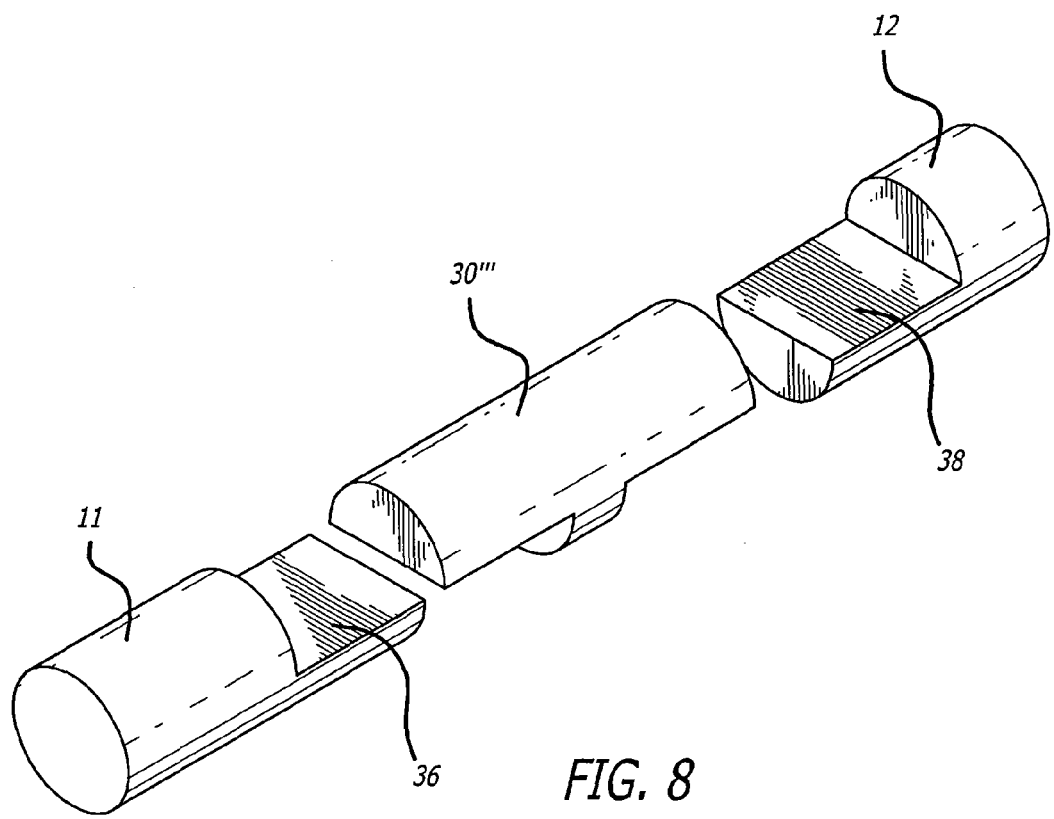
FIG. 8 is a fragmented perspective view of a portion of the guide wire of FIG. 7, showing a connection between proximal and distal portions.

In yet a further alternative embodiment, exemplified in FIGS. 7 and 8 (with similar advantages of the embodiment of FIGS. 5 and 6), the transition piece 30''' may be shaped to connect the outer metal portions 11, 12 which have in turn been shaped to provide a connection between a horizontal surface 36 of the proximal portion 11 and an adjacent non-opposing horizontal surface 38 of the distal portion 12. A profile view of the transition piece 30''' gives the appearance of a "T" shape. It will be appreciated that a combination of the various features of transition piece 30, 30', 30" and 30''' may be used.

After the proximal and distal portions are thus connected, the guide wire may be cleaned in the vicinity of the connection by known means such as electropolishing, brushing, or grinding to remove any slag or minor rough spots.

An advantageous characteristic arising from forming the transition piece 30 of nickel, or a mild alloy of nickel, is that, compared with vanadium which is known to be a successful transition piece for welding stainless steel to nitinol generally, nickel has a lower melting point than vanadium. Thus, the microwelding process would tend to impart less heat to the distal portion of the guide wire than vanadium would require, and is therefore more suitable for microwelding as it is less likely to alter the beneficial characteristics of the nitinol alloy (such as the amount of pseudo-elasticity and the phase transition temperatures) in the process of welding.

Another advantageous feature of nickel is that it has a higher coefficient of thermal expansion than vanadium, and thus is better matched with the higher coefficient of thermal expansion of the stainless steel proximal portion, and of the distal nitinol portion. Accordingly, during heating or cooling of the weld in this case, less volumetric expansion or contraction differential may occur at the boundaries between the transition piece and the proximal and distal portions, and consequently, there is less tendency for cracking or locked-in stresses to form at the boundaries.

The resulting guide wire presents a uniform outer profile, allowing free movement of catheter elements along the guide wire during operation. In the context of microwelding workpieces as small as those of an intraluminal guide wire (i.e., less than 0.040 inches), the solution of interposing a welded transition piece formed essentially of nickel between a stainless steel portion and a nitinol portion achieves adequate strength and flexibility.

Guide wires contain a central wire "core" which runs distally from their proximal end. In one design type ("core-to-tip"), the core wire extends all the way to the very tip of the product, and several cm at the distal end of the core wire is purposely flattened. In another type ("shaping ribbon" design) depicted in FIG. 1, the core extends to a distal location somewhat shy of tip and another flattened wire component extends to the very tip. In the latter instance, the core and adjacent shaping ribbon are joined together, usually within a solder or braze joint that includes a short section of the surrounding tip coil and/or intermediate coil. This "center solder" joint provides axial continuity to the product so its tip region will not distend if the user pulls the proximal shaft while the tip is lodged within the vasculature.

Core-to-tip designs are usually comprised of a single core wire material, typically stainless steel. After the distal end is ground to a prescribed profile, several cm is flattened to produce an integral shaping ribbon. The tip of the core wire is soldered to the distal end of the tip coil, so the core wire runs all the way to the guide wire tip. The physician usually bends the distal section to an "L" or "J" shape so that the guide wire can be steered more effectively. Shape retention of the flattened distal core depends upon both its dimensions and its material properties. Although the stainless steel wire used in guide wires is highly cold worked in order to have high yield stress (about 300,000 psi), the elastic modulus of stainless steel is inherently high (about 28,000,000 psi), so its elastic strain limit is only about 1% (i.e., yield stress/elastic modulus). This means that strain values exceeding about 1% results in permanent deformation. While degree of elasticity makes it relatively easy for the user to shape the distal end of the guide wire for steering, it can be problematic: during a challenging case the shape can become severely distorted, adversely affecting its subsequent performance.

Materials having a greater elastic strain limit inherently perform better than stainless steel with regard to shape retention. For example, cold-worked linear elastic nitinol has a more favorable combination of high yield stress and low elastic modulus and thus requires greater strain to induce permanent deformation (up to 3%). Another example is certain beta-titanium alloys, which similarly have high yield stress and low modulus (about 2%-3%). A shaping ribbon made of either type of material would of course be more difficult to impart an initial shape, but once set the shape would be more difficult to distort in service. It should be noted that conventional superelastic nitinol, which has an abnormally high elastic strain limit (about 8%) would not generally be suitable, because it is so resilient that the physician would experience extreme difficulty imparting a shape.

The proximal ends of guide wires are typically made of stainless steel. Having a relatively high elastic modulus means that the proximal shafts are reasonably stiff in both bending and torsion. However, it may be advantageous to employ a stiffer material for the proximal shaft, either for enhanced support or for improved torque transmission. In that case, a high elastic material such as tungsten or, preferably, a tungsten-rhenium alloy such as W-25Re, could be used for the proximal shaft. Tungsten and tungsten-rhenium alloys have elastic moduli that are nearly double that of stainless steel, which may be too stiff for the distal portion of a guide wire. Thus, it may be advantageous to employ a very high modulus material for the proximal shaft, medium modulus (or superelastic) material for the ground distal section, and a material having high elastic strain limit for the distal "ribbon" section.

The present invention contemplates such design options as depicted in a preferred embodiment in FIG. 9. The core-to-tip guide wire 100 has multiple, independent core portions 102, 104, 106 that are joined together during fabrication. Specifically, the guide wire 100 has a discrete, proximal, high modulus core portion 106 with proximal and distal ends made of a first material; a discrete, intermediate, medium modulus core portion 104 with proximal and distal ends, wherein the proximal end is joined to the distal end of the proximal core portion, made of a second material; and a discrete, shapeable, low modulus distal core portion 102 made of a third material, having a flattened, shapeable section 108 at a most distal end that is not welded to but is made from the same third material as the shapeable distal portion 102, and wherein the flattened, shapeable section 108 can be permanently deformed by finger pressure to create a tip that can be steered through a patient's vasculature. As seen in FIG. 9, the very distal tip of shapeable distal portion 102 can be bent or deformed into a "J," "L," or like bend 112. FIG. 9 further depicts a plurality of weld zones 110 joining the discrete core portions 102, 104, 106 together with the weld zone outside diameters blended into the outside diameters of the respective core portions. A tip coil 114 is disposed over the distal core portion 102.

The weld zones 110 represent welding multiple core segments or portions 102, 104, 106 of wire end-to-end, preferably by, but not limited to, the butt welding methods described in greater detail below. After welding, the wire assembly is ground at its distal end 108 to produce a profile similar to that of a conventional guide wire core. The distal end 108 would typically then be flattened to produce a non-circular cross-section in a manner similar to that of a core-to-tip guide wire core. Upon assembly into a finished guide wire, the flattened distal region of the core provides a shapeable section for the physician to create a custom bend or curve 112 to enable guide wire steering. This most distal section 102 of the core would be made of a shapeable but resilient material (such as cold worked stainless steel or cold-worked linear-elastic nitinol or a beta titanium alloy possessing high yield strength and low modulus or other suitable material possessing high elastic limit). The adjacent section 104 may be superelastic nitinol wire for high resiliency and the proximal section 106 made of stainless steel. Alternatively, the adjacent section may be entirely stainless steel for greater catheter support or overall torque transmission. Or, the adjacent section may be made of a material with greater elastic modulus than stainless steel for even greater support or torque transmission. Or the adjacent section may be entirely superelastic nitinol for improved overall resiliency. It is preferred in this embodiment that the most distal core segment 102 is made from a shapeable, resilient material and that it extends to the guide wire tip 108 to create a core-to-tip design.

One method for joining the stainless steel proximal wire segment to the superelastic nitinol distal segment involves grinding down the two mating ends and adhesively bonding them in a "double lap" joint using a superelastic nitinol component as a tubular splint. This joint is positioned about 40 cm away from the guide wire tip, where it is unlikely to exit the guide catheter and encounter significant vascular tortuosity. Because of its susceptibility to kinking and due to size limitations, the existing double lap joint method is generally not applicable to more distal locations along the core, where it is ground to substantially smaller dimensions than the approximate 0.013 inch proximal shaft diameter. In short, the present invention expands the design possibilities for guide wires whose cores are comprised of at least two different wire materials.

Another potential advantage that the present invention provides versus a conventional "shaping ribbon" design is that the joint between the distal core segment and its adjacent segment would no longer have to reside within the center solder joint. This is a departure from the conventional shaping ribbon design. As a result, the shapeable distal segment could be shorter than the tip coil. This could improve shape retention, for example, by allowing the length of an adjacent superelastic nitinol segment to be increased at the expense of the distal segment so that the shapeable distal segment is only as long as is necessary for an "L" or "J" shape. This would reduce the risk of inadvertent permanent deformation of the guide wire.

It is desirable to metallurgically join two dissimilar wires together, such as by welding, rather than continue using adhesive joints. Ordinarily, fusion welding of wires in the size range pertaining to guide wires could be readily performed with commercially available welding equipment. However, nickel-titanium alloys ("nitinol") are notoriously incompatible with stainless steel and many other alloys when their constituent elements are melted together. Certain elements, notably the titanium in nitinol, readily form intermetallic compounds with other elements, such as the iron in stainless steel. These compounds are inherently brittle and tend to cause cracking or complete failure within the weld zone at relatively low loads and strain values. Thus, conventional fusion welding methods such as laser welding, electron beam welding, TIG welding, plasma arc welding, flash butt welding, arc percussive welding, etc., are generally considered unsuitable for butt welding nitinol wire to stainless steel or most other materials. The present invention, however, goes against this conventional wisdom as described in more detail below.

There exists several commercial welding processes which are capable of reliably joining dissimilar metals without melting either work piece. All of these methods involve solid state bonding rather than fusion. A metallurgical bond is created while both materials remain in the sold state, typically through the application of heat and pressure at the dissimilar metal interface. The earliest known method, known as forge welding, employs the blacksmith's technique of heating both work pieces near but below their respective melting points and forcing them together via successive hammer blows. This method, of course, is unsuitable for butt welding fine wires together. Another solid state joining method, explosion welding, uses an engineered explosive charge to generate extremely high relative velocity and consequently high interfacial pressure between the work pieces. This method is ideal for laminating sheet and plate materials, but again not for butt welding fine wires.

Another method, resistance welding, drives electrical energy across the interface between two contacting surfaces and, while generally used to produce fusion welds, can in some instances be used to produce solid state welds. However, the tendency for the wire ends to oxidize rapidly upon heating when exposed to air makes solid state welding of nitinol-to-nitinol or nitinol-to-stainless steel by conventional resistance welding methods challenging at best. Great care is required to exclude air or other contaminants from the abutting wire interface during conventional resistance welding.

Yet another commercial welding process, known as friction welding, relies upon the frictional heat generated by rotating one work piece while pressing it against the other. As solid material near the interface heats and softens, it naturally flows radially outward. This flow results in what is known as "upset," and this expelled material adheres to both work pieces and is usually removed afterward. The radial movement of material naturally removes oxides and other contaminants from the original interface, making friction welding an excellent method for butt welding a wide range of dissimilar metals. Commercial friction welding equipment can join bars and tubes down to about one-eighth (⅛) inch in diameter, but as the work piece diameter decreases, the rotational speed must typically be increased in order to maintain the surface speeds (linear speed around the wire periphery) necessary for adequate frictional heating. While commercial equipment designed for one-eighth inch bar can rotate up to 60,000 RPM, a typical coronary guide wire shaft diameter of 0.013 inch would require substantially greater rotational speeds. As a confounding matter, the mating 0.013 inch wires would have to be gripped very near the intended weld interface to maintain proper alignment and to provide sufficient column support, thereby drawing away a substantial amount of frictional heat. Further, abruptly stopping from such high rotational speeds without damaging or destroying the tiny butt weld would be a daunting challenge. In short, butt welding small wires by conventional friction welding is considered unfeasible.

On the other hand, the present invention is a departure from the above-described conventional methods in that it combines elements from resistance welding and friction welding processes into a single, integrated process producing unexpected results. According to a preferred process, resistive heating is used to help raise the temperature at the interface between two abutting wires, while one wire is spun relative to the other at substantially lower speeds than would be necessary in conventional friction welding. This process is unexpectedly well suited for joining dissimilar metals that are usually incompatible by fusion welding, because the wire rotation displaces oxides and other contaminants from the interface. By spinning at relatively low speeds while controlling the axial force and weld energy input, welds could be produced without oxides or melting at the final weld interface. Beneficially, the present invention process can be applied to wire sizes that are too small for conventional friction welding. In particular, it is applicable to the wire sizes typically used in shafts for coronary guide wires (about 0.010-0.020 inch). The present invention processes are a further departure from conventional wisdom for friction welding tiny wire sizes.

In a preferred embodiment, the present invention contemplates using an electronic control system such as a programmable logic controller (PLC), a drive motor to rotate one of the wires, two collets or other means for gripping both wires, adjustable fixturing to axially align the wires, a resistance welding power supply, and a means for controlling the axial force between the wires. The latter can be provided by an off the shelf resistance weld head which, preferably, can also monitor axial displacement during the welding process. A displacement monitoring feature not only quantifies the amount of upset during each weld cycle, but can be used to signal the power supply to shut off after a prescribed amount of upset is reached (for example: Miyachi Unitek Series 300 weld heads). A specific resistance welding power supply capable of accurately controlling via closed loop feedback either current, voltage, or power output is the Miyachi Unitek UB25, a linear DC system designed for miniature weld applications.

One example of how this hybrid welding process might be performed is as follows: (1) rotate one of the wires at a fixed speed; (2) butt the wires together and apply a fixed axial force (pre-weld force) which creates upset material (116, FIG. 9A); (3) begin ramping down the rotational speed; (4) apply greater axial force (weld force); (5) ramp up the resistance weld energy; (6) hold resistance weld energy constant; (7) ramp down the resistance weld energy; (8) rotational speed reaches zero; and (9) weld is completed.

The above sequence may be taken out of order, with steps omitted, or modified, such as by applying the increased axial force (weld force) before ramping down the rotational speed, or by applying greater axial force after resistance weld energy input has begun, or by ramping down the weld energy after the rotational speed has reached zero. It is preferable that the input of weld energy begin while the wire is still being rotated, because it is the combination of heating and rotation that softens and displaces the original interfacial material and thereby eliminates oxides and other contaminants from the initial interface. What is also preferable is that the process is controlled such that, upon removal of upset material 116 from the periphery, the remaining weld 110 contains no melted and re-solidified material.

As an alternative to ramping down the rotational speed while applying resistance weld energy, the rotational speed may be held constant when resistance heating begins. When sufficient interfacial material has been heated and displaced, resistance heating is terminated and the relative rotation of the wires is abruptly stopped. This could be attained by directly stopping the drive motor, by de-coupling the motor via a clutch mechanism and applying a brake to the rotating wire's grip, or by releasing at least one wire's grip. Otherwise, the newly formed weld might be damaged or destroyed by continued rotation as the weld zone cools from its heated, pliable state.

To minimize joint profile, the upset material surrounding the weld zone or region 110 would normally be removed afterward. This could be easily performed by a grinding operation. One way is to simply include the weld region in the distal section of the guide wire core that is centerless ground. Another way is to bring the weld region laterally against a spinning abrasive wheel while gradually rotating the weldment to circumferentially remove the upset material. This could be performed while the weldment is still in the weld apparatus. Another method is to feed the weldment through a close-fitting die which shears off the upset material. Other techniques, of course, could also be used.

While a particular form of the invention has been illustrated and described, it will also be apparent to those skilled in the art that various modifications can be made without departing from the spirit and scope of the invention. Accordingly, it is not intended that the invention be limited except by the appended claims.

We claim:

1. A multi-segment intravascular guide wire, comprising:
   a discrete, proximal, high modulus core portion with proximal and distal ends made of a first material selected from the list consisting of stainless steel, tungsten, or tungsten-rhenium alloy and having a first outer diameter;
   a discrete, intermediate, medium modulus core portion with proximal and distal ends, wherein the proximal end is joined to the distal end of the proximal core portion, the intermediate core portion being made of a second material of superelastic nitinol and having a second outer diameter;
   a discrete, shapeable, low modulus distal core portion made of a third material selected from the list consisting of cold worked stainless steel, cold worked linear elastic nitinol, or beta titanium and having a third outer diameter; and
   a plurality of weld zones formed by resistance welding, joining the discrete core portions together, the weld zones having outer diameters equivalent to the first, second and third outer diameters of the respective core portions.

2. The intravascular guide wire of claim 1, wherein the distal core portion having a flattened shapeable section at a most distal end that is not welded to but is made from the same third material as the shapeable distal portion.

3. The intravascular guide wire of claim 2, wherein the flattened, shapeable section is permanently deformed by finger pressure into at least one of an "L" shape and a "J" shape.

4. The intravascular guide wire of claim 2, wherein the flattened, shapeable section is permanently deformed by finger pressure up to a bending strain of about 3% at its outer surface.

* * * * *